United States Patent [19]
Danon

[11] Patent Number: 6,146,890
[45] Date of Patent: *Nov. 14, 2000

[54] METHOD AND SYSTEM FOR CULTIVATING MACROPHAGES

[76] Inventor: David Danon, 83/8 Hagalil Street, Ganei Tiqva 55900, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,307

[22] PCT Filed: Jun. 30, 1995

[86] PCT No.: PCT/US95/08351

§ 371 Date: Mar. 21, 1997

§ 102(e) Date: Mar. 21, 1997

[87] PCT Pub. No.: WO96/01045

PCT Pub. Date: Jan. 18, 1996

[30] Foreign Application Priority Data

Jul. 3, 1994 [IL] Israel ........................................ 110195

[51] Int. Cl.[7] ................................ C12N 5/00; C12N 5/02; C12N 5/08
[52] U.S. Cl. .............................. 435/377; 435/2; 435/325; 435/372; 435/378; 435/408
[58] Field of Search ................................ 435/372, 2, 366, 435/374, 283.1, 294.1, 93.7, 93.71, 377, 378; 604/407, 408, 409

[56] References Cited

U.S. PATENT DOCUMENTS

| | | | |
|---|---|---|---|
| 4,004,587 | 1/1977 | Jess ..................................... | 128/214 R |
| 4,246,344 | 1/1981 | Silver, III .................................. | 435/39 |
| 4,361,148 | 11/1982 | Shackleford et al. .............. | 128/214 D |
| 4,374,644 | 2/1983 | Armstrong ................................ | 436/63 |
| 4,757,017 | 7/1988 | Cheung .............................. | 435/240.23 |
| 4,829,002 | 5/1989 | Pattillo et al. ........................ | 435/297.1 |
| 4,919,823 | 4/1990 | Wisdom ................................... | 210/749 |
| 4,937,194 | 6/1990 | Pattillo et al. ........................ | 435/240.2 |
| 4,946,434 | 8/1990 | Plaisted et al. ............................ | 494/29 |
| 4,997,762 | 3/1991 | Hanna, Jr. et al. ................. | 435/240.27 |
| 5,070,012 | 12/1991 | Nolan et al. ................................. | 435/6 |
| 5,098,371 | 3/1992 | Juji et al. ..................................... | 604/4 |
| 5,141,486 | 8/1992 | Antwiler .................................. | 494/37 |
| 5,192,553 | 3/1993 | Boyse et al. ............................. | 424/529 |

FOREIGN PATENT DOCUMENTS

| | | |
|---|---|---|
| 1270467 | 6/1990 | Canada . |
| 9412156 | 6/1994 | WIPO . |

OTHER PUBLICATIONS

David Danon, et al., Promotion of Wound Repair in Old Mice by Local Injection of Macrophages, Proc. Natl. Acad. Sci. USA, vol. 86, pp. 2018–2020, Mar. 1989.

Lopez et al., J. Innumother., 11:209–217, 1992.

Niskanen et al., J. Clin. Invest., 65:285–289, 1980.

Weiss, In "The Blood Cells and Hematopoietic Tissues", Second Edition, Elsevier, pp. 447–448, 1977.

*Primary Examiner*—Michael G. Wityshyn
*Assistant Examiner*—Janet M. Kerr
*Attorney, Agent, or Firm*—Ladas & Parry

[57] ABSTRACT

A method of cultivating macrophages from blood, including collecting a quantity of blood, fractionating the quantity of blood into a plasma fraction, a white blood cell fraction generally including monocytes, and a red blood cell fraction, segregating the white blood cell fraction from the plasma fraction, while allowing a portion of the red blood cell fraction to remain mixed with the white blood cell fraction, the portion of the red blood cell fraction being less than the white blood cell fraction, and inducing differentiation of the monocytes into macrophages and lysing at least part of the portion of the red blood cell fraction mixed with the white blood cell fraction by causing an osmotic shock to the white blood cell fraction and the red blood cell fraction

5 Claims, 1 Drawing Sheet

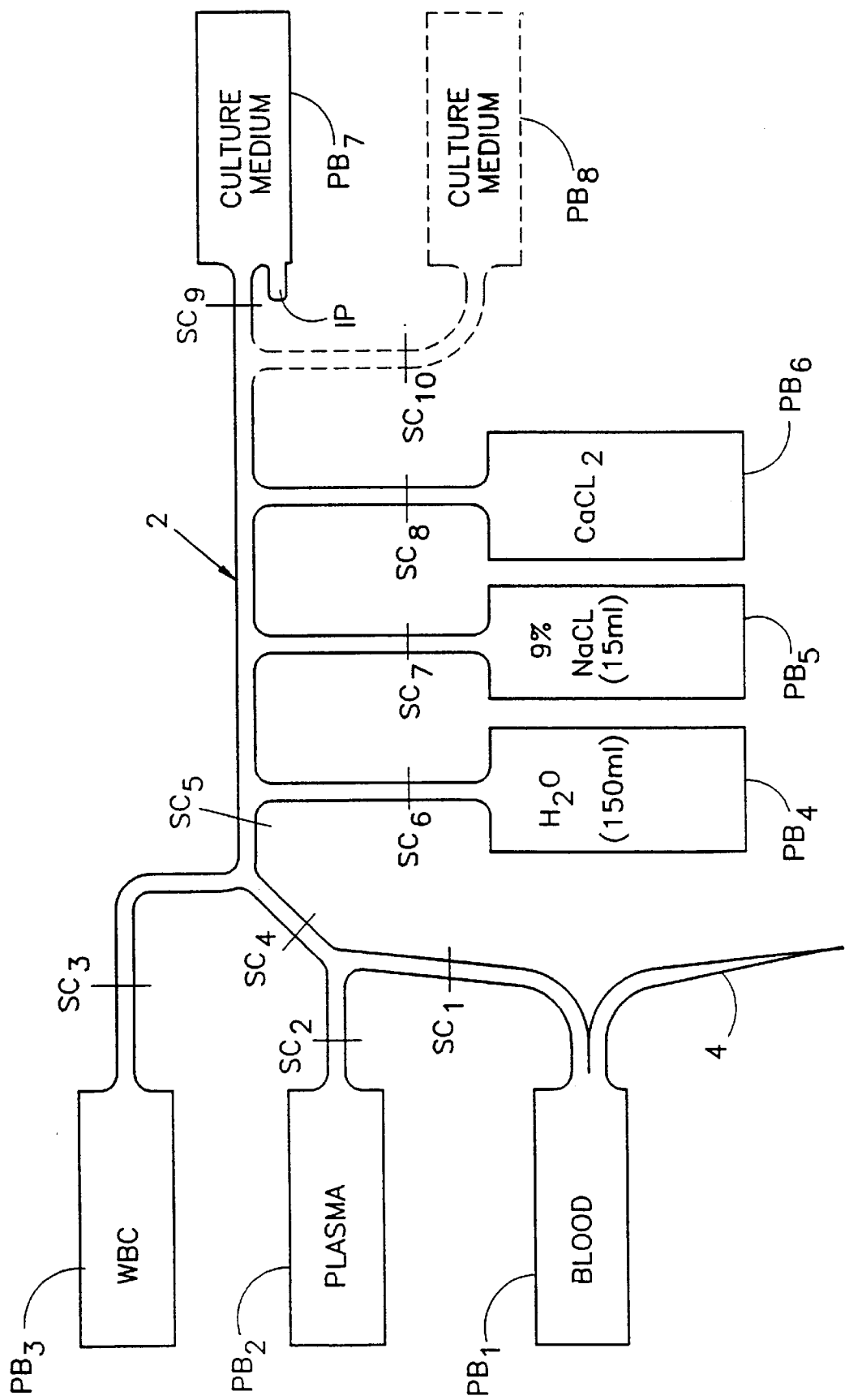

METHOD AND SYSTEM FOR CULTIVATING MACROPHAGES

The present invention relates to a method and system for cultivating cells. The method and system are particularly useful for growing macrophages from human blood, and are therefore described below with respect to this application.

BACKGROUND OF THE INVENTION

Macrophages, namely phagocytic cells phagocytize and digest old and deteriorated red blood cells, bacteria and other microscopic particles. They have been found to play an important role in wound repair. They produce substances that stimulate proliferation of fibroblasts, the synthesis of collagen by fibroblasts, and other elements that are necessary for wound healing. For example, it was found that wound repair could be accelerated in old mice by application of the wounds of macrophages derived from peritoneal fluids of young mice (D. Danon, M. A. Kowatch and G. S. Roth, Proc. Natl. Acad. Sci. USA, Vol.86, pp.2018–2020, March 1989).

The present methods of preparing macrophages out of blood monocytes are complicated, expensive, time-consuming and difficult to apply routinely, because they require considerable specialized labour, expensive disposable materials, and specialized laboratory facilities. Moreover, the present techniques involve a significant risk of contamination during preparation and therefore require regular testing to assure the absence of bacterial infection in the resulting suspension of macrophages.

SUMMARY OF THE INVENTION

An object of the present invention is to provide a method and system for growing cells, particularly, macrophages, which have advantages in the above respects. More particularly, an object of the invention is to provide a method and system for growing cells, particularly macrophages, which do not require specialized labour, expensive disposable materials, or a specialized laboratory, and which reduce considerably the risk of infection.

According to one aspect of the present invention, there is provided a method of cultivating cells present in suspension by subjecting the cells to at least one sterile reagent and cultivating the cells in a sterile culture medium, comprising: placing the cells in suspension, the at least one reagent, and the culture medium in three separate sterile containers; connecting together the containers, and hermetically sealing their contents from the atmosphere, by sterile tubings having fluid flow control devices which may be opened and closed; and opening and closing the fluid flow control devices as required in order to transfer the contents of one container to another, while isolating the container contents from the external environment.

The invention is particularly useful for cultivating macrophages from blood.

Since the complete process can thus be carried out in a completely controlled atmosphere hermetically sealed from the outside atmosphere, there is little risk of infection, and therefore no need for special sterile hoods, laminary flows, and sterile disposable tools. Testing to assure the absence of bacterial infection is not crucial. In fact, not one case of infection was found in 150 preparations of macrophages in accordance with the method of the present invention where every second or third preparation was tested.

According to another aspect of the present invention, there is provided a method of cultivating macrophages, comprising: separating from an initial quantity of blood, a white blood cell fraction which includes a mixture of all kinds of white blood cells and red blood cells having usually a much higher concentration of white blood cells than in the initial quantity of blood; subjecting the white blood cell fraction (buffy coat) to an osmotic shock which is more destructive of red blood cells than white blood cells; re-establishing iso-tonicity in the white blood cell fraction; adding the white blood cell fraction to a culture medium in a container; and incubating the culture medium with the white blood cells fraction.

It has been found that subjecting the white blood cell fraction to osmotic shock and then re-establishing isotonicity therein destroys substantially all the red blood cells and much fewer white blood cells, such that the result is a suspension having a high concentration of white blood cells suitable for cultivation in a container with a culture medium. It has also been found that this osmotic shock treatment of the monocytes in the white blood cells fraction enhances their differentiation into macrophages, as evidenced morphologically.

Preferably, the white cell fraction is subjected to osmotic shock by mixing it with a 15-fold volume of distilled water for a period of 30–90 seconds; a period of 60 seconds has been found particularly effective. The iso-tonicity is also preferably re-established by adding to the white blood cell fraction a hypertonic solution of one tenth of the volume of the distilled water used and ten times the concentration of iso-tonic solution, preferably a 9% solution of NaCl.

According to a further important feature of the invention, a serum prepared from the initial quantity of blood is added to the separated white blood cells in the culture medium. This serum is prepared by separating a desired volume of a plasma from the initial quantity of blood, adding a coagulating agent to the plasma to produce the serum, and then separating the serum from the coagulated plasma. Prior procedures for preparing macrophages introduced fetal calf serum or pooled human serum but there is a danger that fetal calf serum may cause creation of antibodies against this serum in the treated host, and pooled human serum increases the probability of adding the danger of viral infection. These dangers are avoided by using serum prepared from the same blood from which the white blood cells were separated.

According to a still further aspect of the present invention, there is provided apparatus for cultivating cells present in suspension by subjecting the cells to at least one sterile reagent and cultivating the cell in a sterile culture medium, comprising: a first container for receiving the cells in suspension; a second container for receiving the at least one reagent; and a third container for receiving the culture medium; the containers being connected together and hermetically sealed from the atmosphere by sterile tubings having fluid flow control devices which may be opened and closed as required in order to transfer the contents of one container to another, while isolating the container contents from the external environment.

While it was previously known, as indicated above, that wound repair could be accelerated in old mice by application to their wounds of macrophages derived from peritoneal fluids of young mice, insofar as the applicant is aware it was not known to use macrophages derived from blood for the therapeutic treatment of a living body, and particularly for wound healing.

According to a still further aspect of the present invention, therefore, there is provided a method for the therapeutic treatment of a living body by applying thereto macrophages cultivated from blood.

Further features and advantages of the invention will be apparent from the description below of a specific example of a method of growing macrophages in accordance with the present invention, using a system as illustrated in the single accompanying drawing figure.

BRIEF DESCRIPTION OF THE DRAWING

The FIGURE shows a closed system for differentiating and cultivating macrophages from white blood cells.

DETAILED DESCRIPTION OF THE INVENTION

The following example describes a procedure for growing macrophages out of white blood cells contained in a quantity of human blood as obtained from the blood bank. The described procedure is carried out in a totally enclosed system without exposing the cells or the various media involved in the procedure to the external environment. Before the procedure is started, the system illustrated in the drawing is setup by providing the following containers in the form of flexible plastic bags $PB_1$–$PB_8$: plastic bag $PB_1$, for containing the initial quantity of blood to be processed; plastic bags $PB_2$ and $PB_3$, for receiving a plasma fraction and a white blood cell fraction, respectively, separated from the initial quantity of blood in plastic bag $PB_1$ during the procedure; plastic bags $PB_4$, $PB_5$ and $PB_6$ for receiving distilled water (150 ml), a 9% solution of NaCl (15 ml), and $CaCl_2$, respectively, used as reagents during the procedure; and plastic bag $PB_7$, to contain a culture medium to be used in the procedure. If desired, an eighth plastic bag $PB_8$ may be included also to contain a culture medium. Preferably, plastic bags $PB_7$ and/or $PB_8$ contains an injection port IP (shown only in plastic bag $PB_7$) for injecting one or more additives to the culture medium within that bag, as will be described more particularly below.

All the plastic bags $PB_1$–$PB_8$ are interconnected together by tubings generally designated 2, which hermetically seal the contents of each bag from the atomosphere. The illustrated tubings 2 include a plurality of manual valves, in the form of slide clamps $SC_1$–$SC_{10}$, which may be manually closed in order to seal the contents of each bag from the others, or manually opened in order to permit transfer of the contents of one bag to another during the various stages of the procedure. It will thus be seen that the illustrated system of plastic bags $PB_1$–$PB_8$, interconnected together by tubings 2 having the slide clamps $SC_1$–$SC_{10}$, isolate all the container contents from the external environment while permitting transfer of the contents of one container to another during the various stages of the procedure.

A quantity of human blood is first collected into bag $PB_1$ (containing an anti-coagulant) by venipuncture in the blood bank using a sterile needle 4. Bags $PB_2$ and $PB_3$ are initially empty. The three bags $PB_1$, $PB_2$ and $PB_3$ are introduced into one container of a centrifuge, while the remaining bags $PB_4$–$PB_8$ are introduced into the opposite container of the centrifuge, with all the bags being connected together by tubing 2 and all the slide clamps $CC_1$–$CC_9$ closed. The two centrifuge containers are equilibrated.

The bags are centrifuged for five minutes at 2,500 rpm (1,000 g). This causes the blood within plastic bag $PB_1$ to separate into a plasma fraction, a white blood cell (buffy coat) fraction, and a red blood cell fraction. The plasma fraction is transferred into bag $PB_2$ after opening slide clamps $SC_1$ and $SC_2$ and compressing bag $PB_1$. Then the white blood cell fraction is transferred to bag $PB_3$ after opening slide clamps $SC_1$, $SC_4$, and $SC_3$.

At this stage, a part of the plasma fraction is returned to the red blood cell fraction in plastic bag PB after opening slide clamps $SC_3$, $SC_4$ and $SC_1$. Bag $PB_1$ may then be disconnected near slide clamp $SC_1$ (after sealing the plastic tubing) and returned to the blood bank for use.

The white blood cell fraction now in bag $PB_3$ is a mixture of white blood cells with red blood cells, but having a higher concentration of white blood cells than in the initial quantity of blood.

The white blood cell fraction now in bag $PB_3$ is subjected to an osmotic shock which is more destructive (shock lysis) of the red blood cells than the white blood cells in that bag. This is done by transferring the distilled water (150 ml) in bag $PB_4$ to bag $PB_3$, by opening slide clamps $SC_6$, $SC_5$ and $SC_3$. This should be executed as quickly as possible, by placing bag $PB_3$ flat on a table, with one hand pressing bag $PB_4$ to discharge the water from that bag into bag $PB_3$, and using the other hand for mixing the water with the white blood cell fraction in bag $PB_3$. This mixing is done for a period of between 30 to 90 seconds, best results having been obtained when it is done for 35 seconds. As indicated above, this subjects the white blood cell fraction within bag $PB_3$ to osmotic shock, destroying most of the red blood cells by shock lysis, thereby substantially increasing the concentration of the white blood cells within that bag.

At this point, i.e., after the distilled water has been mixed with the white blood cell fraction in bag $PB_3$ for exactly 35 seconds, the 9% NaCl solution in bag $PB_5$ is introduced into plastic $PB_3$, by opening slide clamps $SC_7$, $SC_5$ and $SC_3$, and closing slide clamp $SC_6$ and squeezing bag $PB_5$ to discharge its contents into bag $PB_3$. The NaCl solution thus introduced into bag $PB_3$, being a hypertonic solution, re-establishes iso-tonicity in the white blood cell fraction in bag $PB_3$.

At this time, the 12 ml of 20 mM $CaCl_2$ solution in bag $PB_6$ is transferred to the plasma fraction in bag $PB_2$, by opening slide clamps $SC_8$, $SC_5$, $SC_4$ and $SC_2$; all the other clamps are closed. The $CaCl_2$, an agent enabling coagulation, starts the coagulation of the plasma. The plasma fraction in $PB_2$ may then be placed into a deep freezer, while the rest of the bags hang outside, for ten minutes and then removed. This procedure causes the permeation of the blood platelets with respect to the membranes, and the release of the platelet-derived growth factors. The plasma bag is now placed in a 37° C. water bath for 30 minutes to complete the coagulation. If the coagulation is not complete by this time, which would be apparent from the appearance of the contents of the bag, the bag is returned to the 37° C. water bath until coagulation is completed.

Slide clamps $SC_7$ and $SC_8$ are then closed, and bags $PB_5$ and $PB_6$ may then be removed after sealing the plastic tubing near the clamps.

The bag system is then centrifuged at 1,500 rpm (580 g) for five minutes. This sediments the coagulated part of the plasma in bag $PB_2$, leaving the serum as supernatant. It also sediments the white blood cells in bag $PB_3$. The supernatant liquid in the latter bag is transferred to bag $PB_4$, by opening slide clamps $SC_3$, $SC_5$ and $SC_6$. Bag $PB_4$, which originally contained the distilled water, now serves as a sink for receiving the shock lysed cells and the hemolysate in the liquid transferred from bag $PB_3$, whereas the white blood cells and the few red blood cells that resisted the osmotic shock remain in bag $PB_3$.

The culture medium in bag $PB_7$ is now transferred to bag $PB_3$, by opening slide clamps $SC_9$, $SC_5$ and $SC_3$ to resuspend the white blood cells in bag $PB_3$. Cell aggregates are dispersed by manipulating bag $PB_3$, and the suspension is then transferred back to the culture bag $PB_7$.

The serum in bag $PB_2$ separated by the centrifugation is introduced into the liquid culture medium in bag $PB_7$ in an amount constituting 10–100% of the volume of the culture medium. Preferably, the culture medium is RPMI (Rosewell Park Memorial Institute). If e.g., 60 ml of RPMI is in the culture bag $PB_7$, approximately 6 ml of serum is added to that bag from the plasma bag $PB_2$. This is done by opening slide clamps $SC_2$, $SC_4$, $SC_5$ and $SC_9$. At this stage bags, $PB_2$ and $PB_3$ can be disconnected by sealing the plastic tubing near slide clamp $SC_5$.

The injection port IP of culture medium bag $PB_7$ is then cleaned with ethanol, and an antibiotic mixture of penicillin plus streptomycin including buffer (HEPES), is injected by means of a 5 ml syringe with an 18 G needle via the injection port IP. The syringe is removed, but the needle is retained in the injection port IP and is used for injecting sterilized air into bag $PB_7$ by means of an inflating pump that injects the air through an 0.2 micron pore filter, until the bag reaches a thickness of about 3 cm to 4 cm.

The foregoing procedure up to this point usually takes about three hours. The culture bag is then introduced into a 37° C. incubator and retained there for at least ten hours, preferably about 20 hours.

After incubation, the supernatant of the culture bag $PB_7$ is transferred into the empty plastic bag $PB_4$, serving as a sink. The culture bag $PB_7$ now contains substantially only the adherent cells. These are the white blood cells or monocytes, that have already acquired morphological characteristics of macrophages, e.g., spindle-shape cells, triangular cells and pseudopods protruding from cells.

About 10 ml of fresh culture medium at 37° C. is then introduced from culture bag $PB_8$ into culture bag $PB_7$, and the adherent cells in the latter bag are gently rinsed by tilting the bag several times to detach cells that are sedimented but not adherent. This rinsing liquid is then transferred into the "sink" bag $PB_4$. The rinsing procedure is repeated.

The number of macrophages that are adherent to the inner surface of the plastic bag $PB_7$ are estimated under an inverted microscope (objective 20, occular 15). At this magnification, the number of macrophages in the bag is equivalent to about 40,000 times the number of macrophages observed within the microscope field (i.e., there are about 40,000 microscope fields on the internal surface of the bag $PB_7$ in this particular case). Thus, if the field contains 400 macrophages for example, it can be estimated that there would be about sixteen million macrophages within the bag. The rinsing fluid is now transferred to bag $PB_4$.

If it is desired to have about two million macrophages per ml, about 8 ml of RPMI would be transferred to bag $PB_7$ from bag $PB_8$.

At this stage, the culture bag $PB_7$ is applied to a metallic cold plate at a temperature of about 4° C. This causes the adherent macrophages to detach from the inner surface of bag $PB_7$. In order to accelerate the detachment of the macrophages, a glass plate is applied over the bag to sandwich the bag between the glass plate and the cold plate while the two plates, and the bag in between, are tilted back and forth several times to produce a mechanical agitation of the liquid within the bag. This procedure takes about 30 minutes.

The cells can now be removed from the bag by using a disposable sterile syringe and needle via the injection port IP. A few drops may be used for counting the macrophages, and according to the results, the macrophages may be concentrated if desired by centrifugation in a sterile, disposable test tube.

While the above procedure describes one example of a method for making macrophages from human blood, it will be appreciated that many variations may be made. For example, hypertonic solutions other than NaCl, coagulating agents other than $CaCl_2$, and liquid culture media other than RPMI, may be used. Also, other techniques could be used for the initial separation of the white blood cells, e.g., by filtration or by leucophoresis. Further, it was found that if during the incubation period (at least ten hours, preferably 20–24 hours) at 37° C., if the temperature is raised to 41° C. for at least one hour (preferably 1.5 hours) during the early part of the incubation period, a "heat shock" was produced which accelerated the differentiation of the monocytes into macrophages.

Another variation would to be include a mixture of 5% $CO_2$ in the sterilized air introduced into the culture bag, instead of simple air. Also, the bag system may be made up of bag sub-systems connected together as necessary by a Sterile Connection Device. For example, the blood collection system $PB_1$–$PB_3$ may be connected to the macrophage processing system of bags $PB_4$–$PB_8$ after separation of the while cells in bag $PB_3$ and disconnection of red cell bag $PB_1$.

Further, while the invention has been found particularly useful for making macrophages, it will be appreciated that the technique and system using containers, tubings and slide clamps which permit the contents of the various containers to be transferred as desired in a closed hermetically-sealed system, may be advantageously used for cultivating other types of cells without danger of infection from the external atmosphere. The tubings used can be connected together by conventional connectors, such as rosettes or other multiple-port connectors.

Still further, certain aspects of the invention can be used independently of other aspects. For example, the method of growing macrophages by the above-described, self-serum and closed-system technique could use other techniques than osmotic shock (e.g., hypertonic exposure, heavy metals, etc.) for inducing differentiation of the monocytes into macrophages. The invention could also be used for growing other types of cells than macrophages.

Many other variations, modifications and applications of the invention will be apparent.

What is claimed is:

1. A method for differentiating monocytes into macrophages comprising the steps of
   a) providing white blood cells including monocytes;
   b) differentiating said monocytes into macrophages by osmotically shocking said white blood cells by mixing said white blood cells with distilled water having a volume greater than that of said white blood cells for a period of about 30–90 seconds, in the absence of an additional differentiation-enhancing substance; and
   c) re-establishing isotonicity in the mixture of said white blood cells and said distilled water by mixing a hypertonic solution with said distilled water and said white blood cells thereby creating an isotonic solution of said white blood cells, said isotonic solution having a saline concentration, said hypertonic solution comprising approximately one tenth of the volume of the distilled water used and approximately ten times the saline concentration of the isotonic solution.

2. The method according to claim 1, wherein said volume of distilled water is approximately 15 times larger than that of said white blood cells.

3. The method according to claim 1, wherein said hypertonic solution comprises a 9% NaCl solution.

4. A method for culturing macrophages from blood comprising the steps of
 a) providing white blood cells including monocytes by separating white blood cells from blood which includes plasma;
 b) placing said plasma and said white blood cells into two separate containers;
 c) coagulating a portion of the plasma of step b) to produce a serum and a coagulated portion of plasma;
 d) removing the serum from the coagulated portion of plasma of step c);
 e) differentiating monocytes into macrophages by osmotically shocking said white blood cells by mixing said white blood cells of step b) with distilled water having a volume greater than that of said white blood cells for a period of about 30–90 seconds, in the absence of an additional differentiation-enhancing substance;
 f) re-establishing isotonicity in the mixture of said white blood cells and said distilled water of step
 e) by mixing a hypertonic solution with said distilled water and said white blood cells thereby creating an isotonic solution of said white blood cells, said isotonic solution having a saline concentration, said hypertonic solution comprising approximately one tenth of the volume of the distilled water used and approximately ten times the saline concentration of the isotonic solution;
 g) centrifuging said isotonic solution of said white blood cells to obtain sedimented white blood cells and a supernatant solution;
 h) removing said supernatant solution from said sedimented white blood cells;
 i) adding said serum of step d) to said sedimented white blood cells of step h) to obtain a suspension of white blood cells; and
 j) culturing said suspension of white blood cells.

5. A method for culturing macrophages from blood comprising the steps of
 a) providing white blood cells including monocytes;
 b) differentiating said monocytes into macrophages by osmotically shocking said white blood cells by mixing said white blood cells with distilled water having a volume greater than that of said white blood cells for a period of about 30–90 seconds, in the absence of an additional differentiation-enhancing substance;
 c) re-establishing isotonicity in the mixture of said white blood cells and said distilled water by mixing a hypertonic solution with said distilled water and said white blood cells thereby creating an isotonic solution of said white blood cells, said isotonic solution having a saline concentration, said hypertonic solution comprising approximately one tenth of the volume of the distilled water used and approximately ten times the saline concentration of the isotonic solution;
 d) centrifuging said isotonic solution of said white blood cells to obtain sedimented white blood cells and a supernatant solution;
 e) removing said supernatant solution from said sedimented white blood cells;
 f) adding a culture medium to said sedimented white blood cells of step e) to obtain a suspension of white blood cells; and
 g) culturing said suspension of white blood cells.

* * * * *